United States Patent [19]

Haessler et al.

[11] 4,130,881

[45] Dec. 19, 1978

[54] SYSTEM AND TECHNIQUE FOR AUTOMATED MEDICAL HISTORY TAKING

[75] Inventors: Herbert A. Haessler, Lincoln; Errol L. Elshtain, Lexington; Taffy Holland, Lincoln, all of Mass.

[73] Assignee: Searle Medidata, Inc., Skokie, Ill.

[21] Appl. No.: 437,052

[22] Filed: Jan. 28, 1974

Related U.S. Application Data

[63] Continuation of Ser. No. 164,690, Jul. 21, 1971, abandoned.

[51] Int. Cl.² ................................................. G06F 9/00
[52] U.S. Cl. ................................................. 364/900
[58] Field of Search .................... 340/172.5; 444/1; 364/900 MS File, 300

[56] References Cited

U.S. PATENT DOCUMENTS

| Re. 27,580 | 2/1973 | Rawson et al. | 364/900 |
| 3,566,365 | 2/1971 | Rawson et al. | 340/172.5 |
| 3,566,370 | 2/1971 | Worthington et al. | 340; 172.5;364/900 |
| 3,747,069 | 7/1973 | Hershberg | 364/900 |

OTHER PUBLICATIONS

Meadow, C. T. & Waugh, D. W., "Computer Assisted Interrogation," Proceeding–*Fall Joint Computer Conference*–1966, vol. 29, pp. 381–394.

*Primary Examiner*—Raulfe B. Zache
*Attorney, Agent, or Firm*—Roy A. Ekstrand

[57] ABSTRACT

An automated medical history taking system and technique wherein selected branch paths through a questioning repertory are provided in accordance with stated patient complaints and wherein medically related questions are automatically propounded even though not specifically selected for review by a patient.

5 Claims, 9 Drawing Figures

WHICH QUESTION SERIES HAVE YOU BEEN INSTRUCTED TO ANSWER ?

FIRST VISIT, FULL REVIEW

FIRST VISIT, DIRECTED REVIEW

RETURN VISIT, FULL REVIEW

RETURN VISIT, DIRECTED REVIEW

SYMPTOMATIC, PHYSICAL REVIEW

DO YOU HAVE A PROBLEM WHICH COULD FIT INTO
A CATEGORY ON ONE OR MORE OF THESE LISTS?
YOU MAY PRESS MORE THAN ONE WHITE BUTTON

LIST 1
ANYTHING IN THIS AREA AND
ALLERGIES
SNEEZING
FAINTING
DIZZINESS
CONVULSIONS
SKIN, ITCHING (ANYWHERE)

LIST 2
ANYTHING IN THIS AREA AND
BLOOD
BRUISES
BREATHING
COUGH
APPETITE
VOMITING
BOWELS
URINE
(EXCEPT BACK)

LIST 3
ANYTHING IN THIS AREA AND
WEAKNESS    TOO HOT
TIRED, SLEEP TOO COLD
SPEECH      FEVER
TINGLING    CHILLS
NERVOUS     ACHES
EMOTIONAL   JUST SICK
(INCLUDE BACK)

LIST 1

LIST 2

LIST 3

A PROBLEM NOT LISTED

NO PROBLEMS

FIG. 3

HERE IS LIST 1. WHICH ARE YOUR PROBLEM AREAS?
YOU MAY PRESS MORE THAN ONE WHITE BUTTON

SKIN, SCALP, HAIR OR FACE

HEADACHES, DIZZINESS, FAINTING, CONVULSIONS

EARS OR EYES

NOSE, MOUTH, THROAT OR NECK

ALLERGIES

FIG. 4

HERE IS LIST 2. WHICH ARE YOUR PROBLEM AREAS ?
YOU MAY PRESS MORE THAN ONE WHITE BUTTON

CHEST, HEART, LUNGS, OR COUGH

BELLY, ABDOMEN, BOWELS, VOMIT OR LIVER

THIRST, KIDNEY, BLADDER OR URINARY

REPRODUCTIVE, PRIVATE PARTS OR BREAST

BLOOD PROBLEMS (ANEMIA, BLEEDING, ETC.)

FIG. 5

HERE IS LIST 3. WHICH ARE YOUR PROBLEM AREAS ?
YOU MAY PRESS MORE THAN ONE WHITE BUTTON

ARMS, LEGS, HANDS, FEET, BACK OR JOINTS

PARALYSIS, WEAKNESS, SPEECH, TINGLING OR TREMBLING

TOO HOT, TOO COLD, GLAND PROBLEM, (THYROID, ETC.)

TIRED, NERVOUS, SLEEP OR EMOTIONAL

JUST FEEL SICK (WEAK, FEVER, CHILLS, ACHES)

FIG. 6

SYSTEM AND TECHNIQUE FOR AUTOMATED MEDICAL HISTORY TAKING

This is a continuation of application Ser. No. 164,690, filed July 21, 1971, now abandoned.

FIELD OF THE INVENTION

This invention relates to automated medical history taking systems and more particularly to a selective branching technique for automated medical history taking to suit individual patient requirements.

BACKGROUND OF THE INVENTION

An automated computer based medical history taking system is the subject of U.S. Pat. No. 3,566,370, assigned to the assignee of the present invention, and provides for efficient development and printout of a patient's medical history. The system includes a display for presenting questions and multiple choice answers to a patient and means for recording patient answers and for selecting subsequent questions for presentation to the patient in accordance with the answers given to previous questions. The system is thus operative in an adaptive manner to develop lines of questioning in accordance with patient answers.

The system includes a repertory of questions and associated possible answers as well as corresponding instructions for the patient, and the questioning process proceeds through the repertory of questions taking various branches in accordance with a patient's answers to previous questions. For some purposes it would be useful to provide multple pathways through the repertory to utilize only portions thereof in particular instances without necessity for answering a group of questions unimportant to a present investigation. For example, during a return visit of a patient who has previously taken an entire medical history, it is usually desirable to presently propound only those questions for updating previous information. In another instance, a patient may be complaining of medical problems with respect to a particular anatomical area, in which case it is desirable to confine the questioning process to that anatomical region.

SUMMARY OF THE INVENTION

In brief, the invention provides a system and technique for selectively employing an entire questioning sequence or portions thereof in accordance with patient requirements and also for providing medically related questions to a patient even though not specifically selected for review. A plurality of major pathways can be selected by a patient through the overall question repertory. In the embodiment of the invention to be described presently, five major pathways are shown for selection through the total question repertory. A major pathway is selected by the patient upon answer to a display which identifies the different question series. The first possible pathway, identified as Initial Visit Full Review, provides a questioning routine through the entire repertory to cover basic social and family history, past illnesses, full symptomatic review of all body parts and physiological systems and psychological review. The second possible pathway, identified as Initial Visit Directed Review, also covers the basic social and family history, past illnesses and psychological review, as with the full review, but covers only a directed symptomatic review of those anatomical areas which the patient indicates are causing difficulties. Thus, during an initial visit to a medical center, a patient may receive a full medical review or a directed medical review depending on his specific requirements.

Additional questioning routines are provided for use with a patient returning for a subsequent medical visit. In one pathway, called Return Visit Full Review, changes in social and family status and in habits are covered, together with full symptomatic and psychologic review. In another alternative pathway, identified as Return Visit Directed Review, the symptomatic review is limited to those anatomical areas which the patient indicates are causing difficulties.

A fifth possible pathway through the questioning sequence, called Symptomatic Physical Review, provides questioning of general heatlh and environmental exposure and psychologic review, but symptomatic review of only those body parts which the patient indicates are of present complaint. In this directed review as with the directed reviews of the alternative pathways described above, the questioning is confined to the anatomical regions of present concern without requiring answers by a patient to questions concerning medical areas about which there is no present complaint.

Of particular importance in the present invention for providing a useful and medically reliable diagnostic tool for use by a physician, pertinent questions are presented to a patient if medically related to a present area of inquiry even though from a nonselected series of questions. For example, even though a patient is being questioned only with respect to complaints involving the head and neck, if he indicates that he is a heavy smoker the patient will see appropriate questions from the lung section although this anatomical region was not specified for questioning. In other words, a medical correlation is provided such that important associative questions will automatically be called forth in response to certain triggering responses by a patient whether or not the patient has specified the anatomical region associated with the associative question.

DESCRIPTION OF THE DRAWINGS

The invention will be more fully understood from the following detailed description taken in conjunction with the accompanying drawings, in which:

FIG. 3 is a representation of a display of symptomatic areas to be selected by a patient for corresponding questioning according to the invention;

FIG. 4–6 are representative of displays of possible symptoms associated with the symptomatic areas of the display of FIG. 3;

DETAILED DESCRIPTION OF THE INVENTION

The system for providing automated medical questioning with which the present invention is employed is described in detail in the above identified U.S. Pat. No.

3,566,370 and the disclosure thereof is specifically incorporated herein by reference. That system includes a console, shown in FIG. 1 herein, having a screen 10 on which are displayed questions and multiple choice answers, controls 12 for selection of one or more answers by a patient, operating controls 14 and a slot 16 for insertion of an identity card containing a patient identification number the insertion of which commences system operation. Questions and associated answers are contained within sections of respective photographic slides such that a particular slide and a particular section of a selected slide are selected for presentation of a question and set of possible responses thereto. Upon answer of a displayed question, the system proceeds to the next question contained within an appropriate slide section for display for answer by the patient, this next question being determined by the answer to previous questions by the patient. The present invention is not limited by the particular instrumentality for presenting questions and answers on the console screen 10, as it will be appreciated that many means for containing questioning information can be provided in a history taking system. For example, questions and associated answers can be arranged in respective frames of a microfiche or on respective frames of a filmstrip rather than in a plurality of slides and slide sections. Or, electronically stored displays can be presented on a cathode ray tube or the like.

Figures 1, 2:
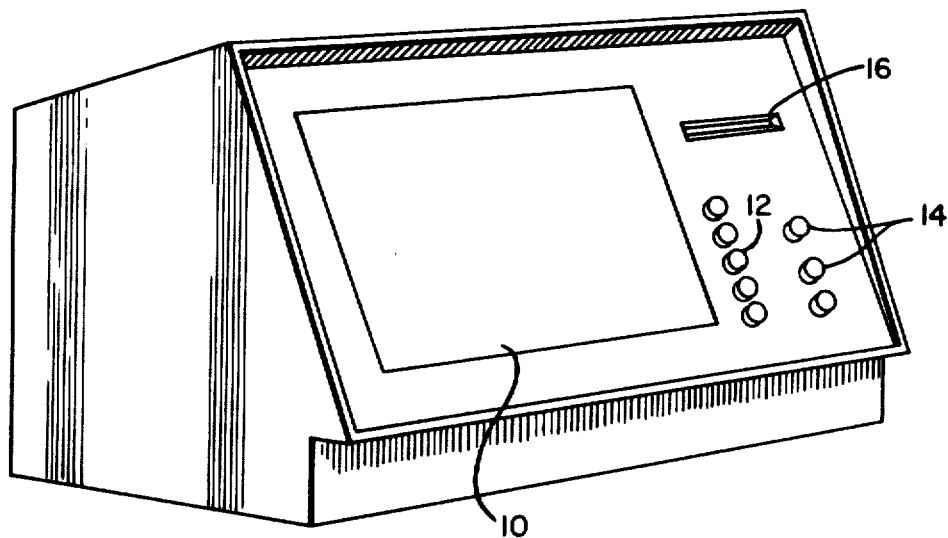
FIG. 1 is a pictorial view of a history taking console useful in practicing the invention.
FIG. 2 is a representation of a display for selecting the particular questioning sequence to be employed according to the invention.

Selection of a desired pathway through the questioning repertory is provided by means of a display question, shown in FIG. 2, which calls for selection by the patient of a particular mode of review. The selected mode of review suitable for a patient's particular purposes can comprise a questioning sequence which may be a complete medical review, a review of particular symptomatic areas, or changes in medical conditions since a previous visit. The several questioning paths are best described in conjunction with the flow chart of FIG. 7.

Figure 7:
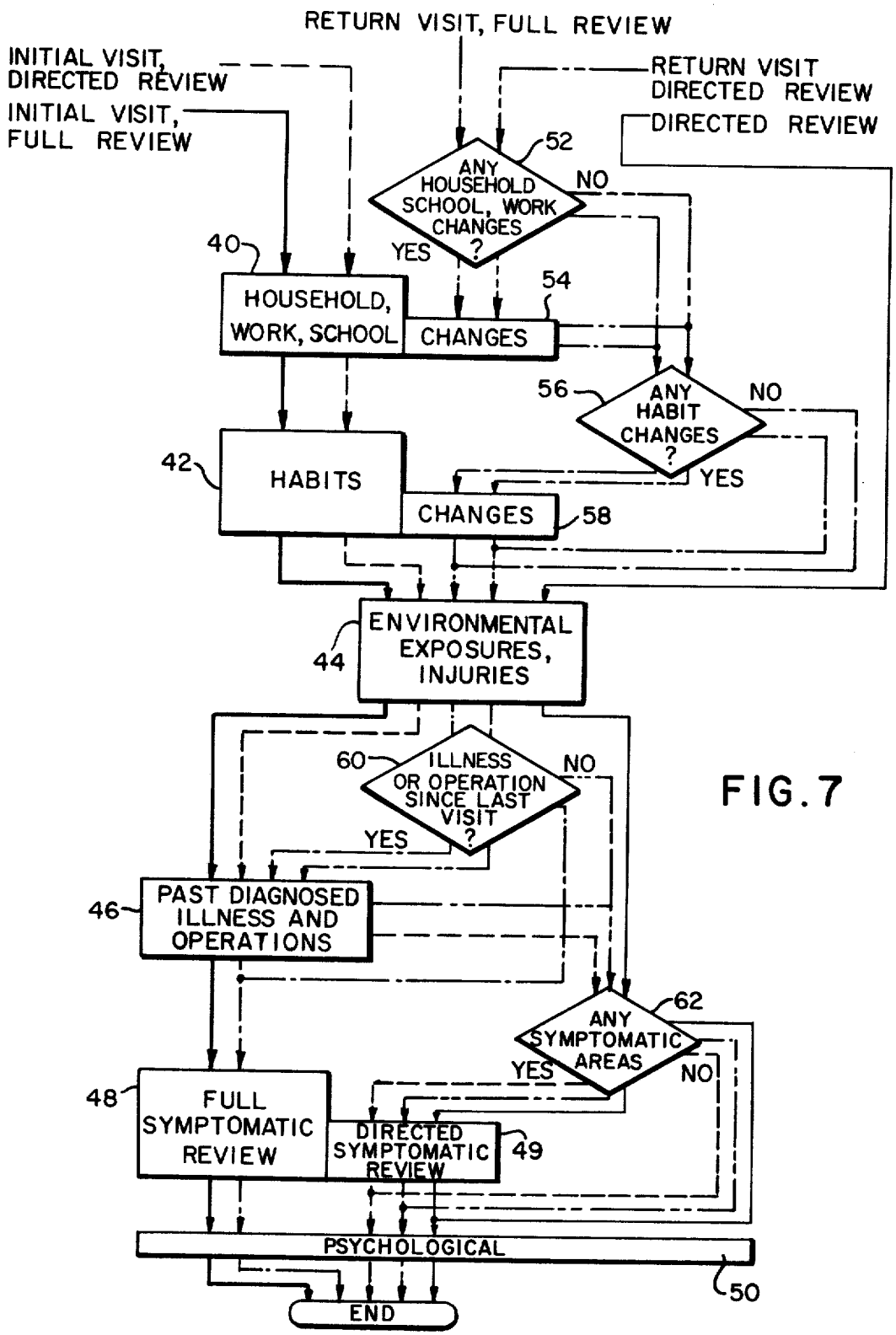
FIG. 7 is a flow chart of the selective branch paths through the questioning sequence provided by the invention.

In discussing the questions and patient answers during consideration of the flow chart of FIG. 7, it will be appreciated that the questions are displayed on console screen 10 for answer by the patient by means of selection of one or more response buttons 12. The apparatus and its operation for providing sequential display of questions and answers is thoroughly described in the above-identified patent to which the reader is referred.

Referring now to FIG. 7 it is seen that each response by the patient to the display of FIG. 2 will direct the patient through a sequence of questions corresponding to one of the five paths illustrated. The first path, Initial Visit Full Review, makes use of the entire question repertory with branching between successive questions being in accordance with answers to previous questions as described in the above patent. Following this path, questions 40 are presented concerning family background and social history, after which a succession of questions 42 concerning the patient's habits such as smoking and drinking are asked. The program then continues to a sequence of questions 44 concerning environmental exposure and injuries and thence to questions 46 concerning past diagnosed illnesses and operations. A sequence of questions 48 is next asked to develop a full symptomatic review concerning the particular patient. A sequence of questions 50 concerning psychological factors is then asked to complete the questioning routine. The first path provides the most complete questioning sequence, the particular number of questions depending upon the patient's answers to previous questions. Normally the entire question repertory will not be used for any one patient.

The second path, Initial Visit Directed Review, is similar to the first path insofar as development of the categories of questions 40, 42, 44 and 46 are concerned. After the questioning sequence 46 on past illnesses and operations, the display of FIG. 3 is presented for answer by the patient to identify symptomatic areas designated by the patient to be of present concern. If in answer to the symptomatic display, the patient indicates no symptomatic areas of complaint, the system will continue to an examination of the psychological factors via the question sequence 50 to complete this testing routine.

If, however, one or more symptomatic areas shown in the display of FIG. 3 are selected by the patient, the system presents those questions associated wit the directed systematic review for the areas selected, as noted by questioning sequence 49. Selection by the patient of List 1 as depicted in FIG. 3 causes subsequent presentation of the display of FIG. 4 which provides an elaborated group of symptoms associated with each answer button 12 on the system console. Similarly, selection of List 2 or List 3 in response to the display of FIG. 3 causes respective presentation of the displays of FIGS. 5 and 6 which set forth corresponding symptoms of possible complaint by the patient. In this manner, the patient is able to select the symptomatic areas of present concern, the system responding to this selection to present only those questions related to the selected symptomatic areas for answer by the patient. At the completion of the question sequence 49, the psychological question sequence 50 is then presented for answer to complete the path. It should be noted that if in response to the display question of FIG. 3 the patient selects a response labeled "a problem not listed", the system will cause the entire symptomatic review to be conducted since the patient did not select any of the directed symptomatic areas in which his problem occurs.

If the patient selects the path identified as Return Visit Full Review or Return Visit Directed Review, a questioning sequence is presented to determine whether changes have occurred since the previous taking of the automated medical history. In either of these paths, a question 52 is presented via the slide display to determine whether there have been any changes in family or social history since a previous visit by the patient. If there have been any such changes, questions 54 are propounded to the patient to identify the particular changes that have taken place since this previous patient visit. A question 56 is then presented to determine whether there have been any changes in habits since the previous visit. If the patient indicates a negative response to question 52, the system then presents question 56 for patient answer. If in response to display question 56 the patient indicates no change in habit, the system causes display of the environmental exposures and injuries questions 44. If, however, the patient indicates an affirmative answer to question 56, then the questions 58 are presented to identify the particular changes.

After the questioning sequence 44, a question 60 is presented to determine whether there have been illnesses or operations since the last visit. If so, then the questioning sequence 46 is displayed for answer to identify the most recent illnesses and operations. If the patient is receiving a full review, the system then presents the questions 48 and 50 to complete the review. If on the other hand, a directed review has been selected by the patient for examination, after a negative answer to question 60 or after answer to questions 46 if question 60 was answered affirmatively, the question 62 (FIG. 3) is shown for selection by the patient of symptomatic areas of present complaint. The directed review then continues in the manner described above.

Upon selection by the patient of the Symptomatic Physical Review, in response to the display of FIG. 2, the questions 44 are immediately presented for answer by the patient, after which the question 62 (FIG. 3) is presented for determination of the selected symptomatic areas for directed review. The directed mode of review is then conducted as above.

The several paths through the questioning sequence provided by the invention achieves an efficient and medically reliable development of a patient history without needless presentation of questions not of concern with respect to the patient's stated medical conditions. By virtue of the invention, medically related questions are, however, always presented for review even though not selected for answer by the patient. As a particular feature of the invention, medically related data is automatically developed in response to certain answers to previous questions. Automatic branching is provided as described immediately below. Two branching techniques are employed in the illustrated embodiment to present triggering questions in response to particular patient answers to previous questions.

Figure 8:
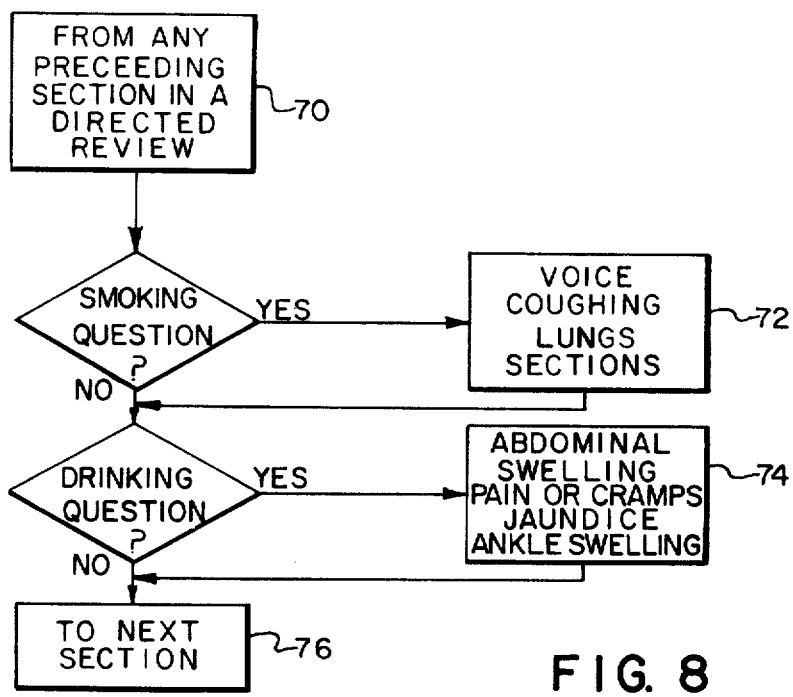
FIG. 8 is a flow chart of an automatic branching routine provided by the invention.

One triggering mode of operation is depicted in FIG. 8. After a predetermined preceding question sequence 70 in a directed review, the system determines whether the smoking question has been answered affirmatively and if so, questions 72 concerning the voice, coughing, and lungs are asked of the patient. If the smoking question was not affirmatively answered, the system proceeds to determination of whether the drinking question has been affirmatively answered. If so, questions 74 with respect to abdominal swelling, pain or cramps, jaundice and ankle swelling are asked, after which the system returns to the next main section of review 76. If the drinking question was not affirmatively answered, the system continues along the normal path to the next questioning section 76. Implementation of this branching technique is typically provided by use of a special entry table in computer memory which notes the identity of the triggering questions. After a predetermined question sequence, such as sequence 70, the special entry table is examined to identify the triggering questions and the patient answers thereto, particular answers causing certain questions to be next presented such as questions 72 and 74. Medically pertinent questions are therefore always called forth for presentation and answer by the patient even though the patient has not scheduled these associated questions.

Figure 9:
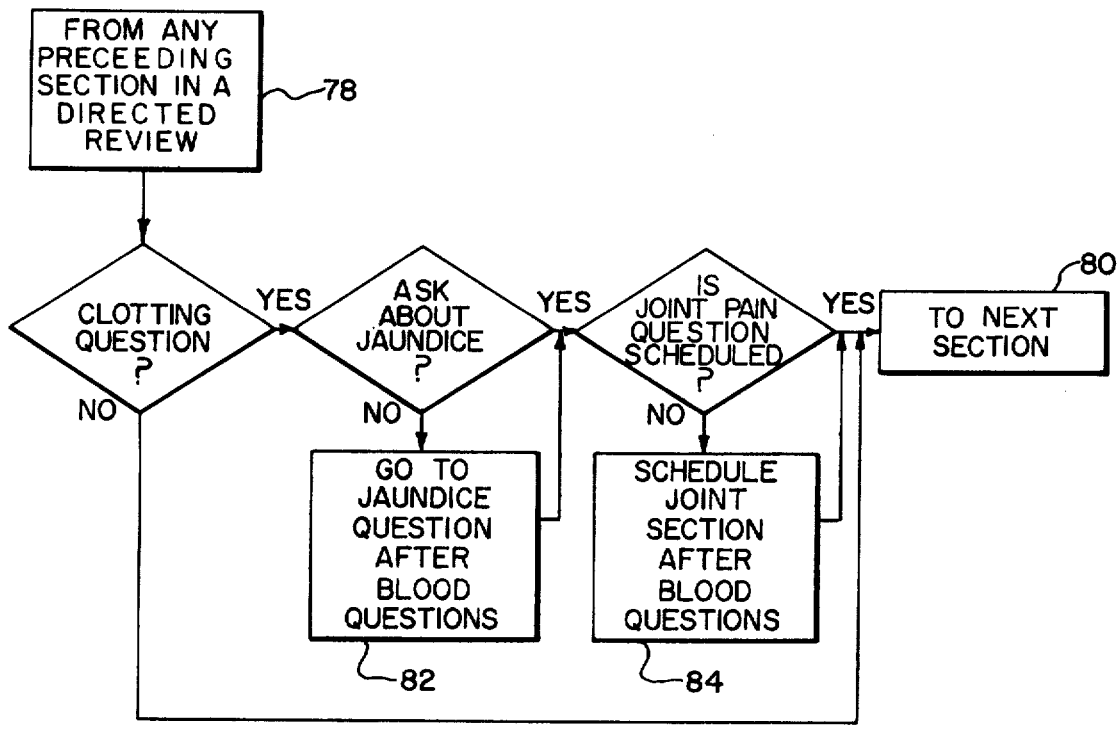
FIG. 9 is a flow chart of another automatic branching routine provided by the invention

In another triggering mode of operation, depicted in FIG. 9, a particular stated problem may suggest that a question from a preceding or following questioning sequence should presently be scheduled for answer by the patient. Referring to FIG. 9, after a predetermined preceding questioning section 78 in a directed review, the system determines whether the patient has indicated clotting problems, by examination of the computer memory to determine whether the clotting question has been answered by that patient. If the patient has negatively answered the earlier clotting question, the system continues along the main questioning branch by proceeding to the next scheduled section of questions 80.

However, if the patient has affirmatively answered the earlier clotting question, the system determines by inspection of the special entry table in memory whether the jaundice question has previously been answered by that patient. If not, the system calls forth the jaundice question 82 at a scheduled point in the questioning sequence. In the illustrated embodiment, the jaundice question is called up for display at the completion of the blood questions, and after answer of the jaundice question the system returns to the main branch path. If the patient has previously answered the jaundice question during the questioning routine, the system does not again call forth the jaundice question since it has been previously answered but proceeds to a determination, again by special entry table interrogation, whether the question respecting joint pains is scheduled. If this latter question is already scheduled, the system continues along the main branch path to the next questioning section 80. If, however, the joint pain question is not presently scheduled, this question sequence 82 is scheduled after completion of the blood questions or at another appropriate point in the questioning sequence. After display and answer to question 84 the system continues to the next question section 80.

As discussed hereinabove, the branching technique for automatically providing medically related data is implemented by use of a special entry table in computer memory. At certain predetermined points in the questioning sequence, the special entry table is examined to determine the identity of triggering questions. The special entry table is masked to a previous question to determine whether or not the previous question was answered. If such a previous question was answered affirmatively, the special entry table causes display of one or more subsequent questions in the manner described in connection with FIGS. 8 and 9. A special entry table location can also be masked to a future question to determine whether or not it is scheduled for answer and if not so scheduled, to then schedule the question for answer at a predetermined time in the question sequence, as described in conjunction with FIG. 9.

The particular branching technique employed depends upon the medical association between previous questions and subsequent questions to be answered. In a typical embodiment, an affirmative answer to a previous question concerning the patient's smoking habits, causes subsequent display of questions with respect to the voice, coughing and lungs and, as described above, these associated questions are presented even though not within a symptomatic area selected for review by the patient. Similarly, an affirmative answer to a question with respect to drinking causes subsequent displays of questions with respect to abdominal swelling, belly pain, jaundice and ankle swelling. Patient answers to questions concerning environmental hazards also trigger the subsequent display of medically related questions. For example, if the patient indicates in answer to an environmental question that he is in regular contact with loud noises, a question will later be presented with respect to possible ear problems. Particular trigger questions are readily changeable within the system by appropriate alteration of the memory table location identifying the triggering questions.

It will be understood that the invention can be implemented by a variety of well known programming techniques and that the invention is not to be limited by what has been particularly shown and described except as indicated in the appended claims.

What is claimed is:

1. In an automated medical history taking system a machine implemented method comprising the steps of:
   presenting a patient selection of a desired questioning routine from a plurality of questioning routines;
   receiving a patient response directing the presentation of a patient-selected one of said questioning routines;
   presenting by stored program control from a processor through a data link a plurality of questions and associated answers comprising said patient selected one of said questioning routines on a patient answer responsive display for developing a medical history of a patient from answers to each of said questions selected by said patient;
   receiving by a data link data representing the selected one or more answers to each of said questions;
   selecting by stored program control responsive to received answers selected by said patient, predetermined ones of said plurality of questions for presentation to said patient to provide a selected mode of review;
   storing data in a memory representative of received answers selected by said patient;
   under stored program control automatically presenting for answer by said patient a question medically related to predetermined ones of said received answers in response thereto even if the medically related question is not one of said predetermined ones of said questions;
   said stored step resulting in a memory stored set of answers which result in a history for said patient.

2. The method according to claim 1 wherein said step of selecting predetermined ones of said plurality of questions includes presenting one or more questions and associated answers representative of symptomatic areas for selection by said patient of a symptomatic area as being of present concern.

3. The method according to claim 1 wherein said step of presenting a plurality of questions and associated answers includes displaying said questions and associated answers on the viewing screen of a console.

4. The method according to claim 10 wherein said automatically presenting step includes the steps of:
   determining from stored data representative of received answers whether a previous question has been answered by said patient; and
   causing presentation of one or more subsequent questions medically related to said previous question in response to a determination that a predetermined answer was received for said previous question.

5. The method according to claim 1 wherein said automatically presenting step includes the steps of:
   determining from stored data representative of received answers whether prederermined answers have been received for predetermined ones of said questions;
   determining whether a medically related question has previously been answered by said patient in response to the determination that said predetermined answer to a predetermined one of said questions has been received; and
   causing presentation of said medically related question to said patient in response to a determination that said medically related question has not previously been answered.

* * * * *